(12) United States Patent
Roncucci et al.

(10) Patent No.: US 8,741,264 B2
(45) Date of Patent: Jun. 3, 2014

(54) SELF-STERILIZING PRODUCTS

(75) Inventors: Gabrio Roncucci, Colle Val d'Elsa (IT); Lia Fantetti, Florence (IT); Giacomo Chiti, Prato (IT); Donata Dei, San Gimignano (IT); Carmela Alongi, San Brancato di Sant'Arcangelo (IT); Annalisa Cocchi, Poggio A Caiano (IT); Valentina Paschetta, Ferrone (IT)

(73) Assignee: Molteni Therapeutics S.R.L., Scandicci (IT)

( * ) Notice: Subject to any disclaimer, the term of this patent is extended or adjusted under 35 U.S.C. 154(b) by 1138 days.

(21) Appl. No.: 11/994,005

(22) PCT Filed: Jun. 29, 2006

(86) PCT No.: PCT/EP2006/063695
§ 371 (c)(1),
(2), (4) Date: Dec. 27, 2007

(87) PCT Pub. No.: WO2007/000472
PCT Pub. Date: Jan. 4, 2007

(65) Prior Publication Data
US 2009/0130049 A1    May 21, 2009

Related U.S. Application Data

(60) Provisional application No. 60/695,752, filed on Jun. 29, 2005.

(30) Foreign Application Priority Data

Apr. 4, 2006 (IT) .............................. FI2006A0089

(51) Int. Cl.
*A61K 31/74* (2006.01)
(52) U.S. Cl.
USPC ...... 424/9.3; 424/78.3; 525/440.03; 540/128; 540/133; 540/123
(58) Field of Classification Search
USPC ...................................................... 424/78.3
See application file for complete search history.

(56) References Cited

U.S. PATENT DOCUMENTS

| | | | |
|---|---|---|---|
| 5,281,616 A | 1/1994 | Dixon et al. | |
| 5,834,455 A | 11/1998 | Russell et al. | |
| 5,965,598 A | 10/1999 | Roncucci et al. | |
| 6,630,128 B1 * | 10/2003 | Love et al. | 424/9.362 |
| 7,144,879 B2 | 12/2006 | Roncucci et al. | |

FOREIGN PATENT DOCUMENTS

| | | |
|---|---|---|
| EP | 0 186 404 A2 | 7/1986 |
| EP | 186404 A2 | 7/1986 |
| EP | 0 906 758 A1 | 4/1999 |
| EP | 906758 A1 | 4/1999 |
| EP | 1 164 135 A1 | 12/2001 |
| EP | 1164135 A1 | 12/2001 |
| EP | 1 356 813 A1 | 10/2003 |
| EP | 1356813 A1 | 10/2003 |
| EP | 1381611 B1 | 1/2004 |
| WO | WO 02/090361 A1 | 11/2002 |
| WO | WO 03/037902 A1 | 5/2003 |

OTHER PUBLICATIONS

Ben-Hur, E. and Rosenthal, I. 1985 "The phthalocyanines: a new class of mammalian cells photosensitizers with a potential for cancer phototherapy" *Int J Radiat Biol* 47:145-147.
Ben-Hur, E. and Rosenthal, I. 1985 "The phthalocyanines: a new class of mammalian cells photosensitizers with a potential for cancer phototherapy" *Int J Radiat Biol Relat Stud Phys Chem Med* 47:145-147.
Dummin, H. et al. (1997) "Selective photosensitization of mitochondria in hela cells by cationic zn(II) phthalocyanines with lipophilic side-chains" Journal of Photochemistry and Photobiology B: Biology 37:2319-229.
Fabris et al. 2005 "A novel tetracationic phthalocyanine as a potential skin phototherapeutic agent" *Experimental Dermatology* 14: 675-683.
Griffiths, J. (1997) "Some observations on the synthesis of polysubstituted zinc phthalocyanine sensitisers for photodynamic therapy" Dyes and Pigments 33:65-78.
Hongjian et al. (1996) "Studies of the supramolecular system of prophyrin-phthalocyanine formed by molecular self-assembly and its photoinduced electron transfer process" Acta Physico Chimica Sinica 12:44-48.
Mao et al. 1998 "Molecular deposition film of porphyrin and pthalocyanine bearing oppositely charged substituents" *Science in China* (Series B) 41:449-454.
Minnock, A. et al. (1996) "Photoinactivation of bacteria. Use of a cationic water-soluble zinc phthalocyanine to photoinactivate both gram-negative and gram-positive bacteria" Journal of Photochemistry and Photobiology B: Biology 32:159-164.
Wohrle, D. et al. (1990) "Synthesis of positively charged phthalocyanines and their activity in the photodynamic therapy of cancer cells" Photochemistry and Photobiology 51:351-356.
Soncin, Marina et al. 2002 "Approaches to selectivity in the Zn(II)-phthalocyanine-photosensitized inactivation of wild-type and antibiotic-resistant *Staphylococcus aureeus*" Photochem Photobiol. Sci 1: 815-819.
Chiti, G. et al. 2005 "In vitro photosensitizing efficacy of cationic phthalocyanine derivatives against *C.albicans:* effect of serum albumins" *Journal of Porphyrins and Phthalocyanines* 9: 463-469.

* cited by examiner

*Primary Examiner* — Michael G Hartley
*Assistant Examiner* — Sean R Donohue
(74) *Attorney, Agent, or Firm* — Knobbe, Martens, Olson & Bear, LLP

(57) ABSTRACT

Self-sterilising products, and in particular novel products comprising phthalocyanine derivatives bound to polymers, a process for the preparation of said products and their use for preparing self-sterilising industrial and medical articles or devices, are described.

11 Claims, 1 Drawing Sheet

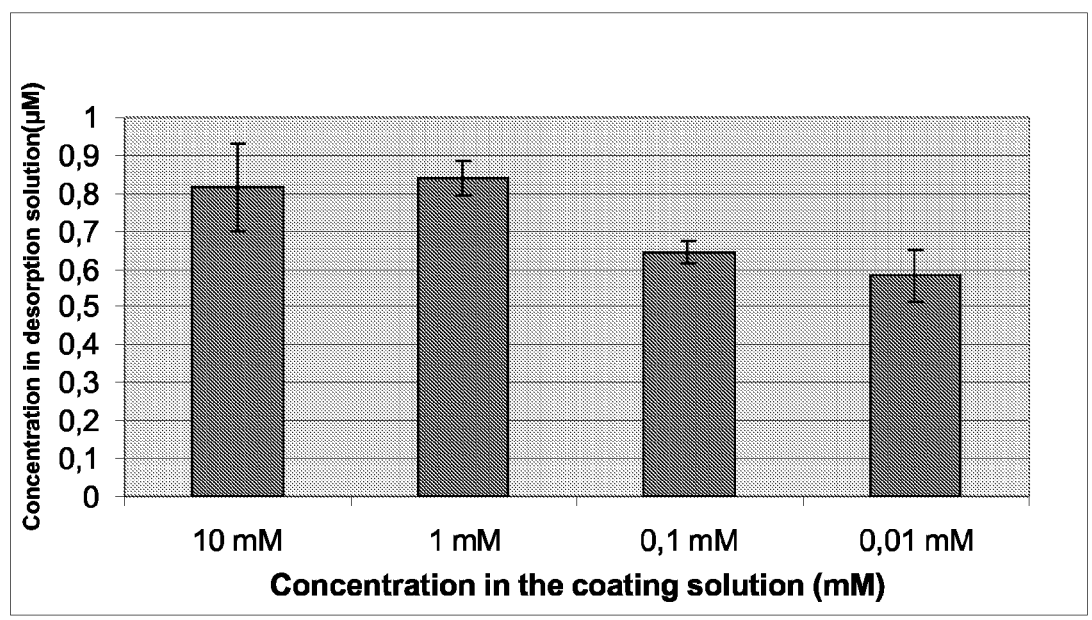

SELF-STERILIZING PRODUCTS

This application is U.S. National Phase of International Application PCT/EP2006/063695, filed Jun. 29, 2006 designating the U.S., and published in English as WO 2007/000472 on Jan. 4, 2007, which claims priority to U.S. Provisional Application No. 60/695,752 filed Jun. 29, 2005 and Italian Patent Application No. FI2006A000089 filed Apr. 4, 2006.

FIELD OF THE INVENTION

The invention relates to the field of phthalocyanine derivatives, and in particular to new products having self-sterilising properties in which the phthalocyanine derivatives of general formula (I), given hereinafter, are bound to polymers.

STATE OF THE ART

In human, many infections are transmitted by contact. This is particularly true for infections connected to the use of medical devices such as catheters, implants, plastic contact lenses and the like. Indeed, in nearly all cases, the micro-organisms responsible for these infections, which have grown on the xenogenic materials of the device, are particularly virulent and resistant to inactivation by standard treatments and by antibiotics in current use.

It is generally known that resistance to antibiotics has developed in a growing number of micro-organisms, which is worrying both for the medical profession and population. Furthermore, there are concerns as to whether new antibiotics can be rapidly and effectively developed to prevent possible problems in the future. As is known, the development of new antibiotics is a very expensive and lengthy process, during which time micro-organisms become resistant more and more quickly under evolutionary pressure in the presence of new antibiotics based on known mechanisms of action.

Continuous research is therefore under way on new active principles and alternative methods able to eradicate the causative microbial agents.

For the sterilisation of medical articles and devices, known methods include a variety of treatments, such as treatment with cytotoxic substances in gaseous form or as solutions, exposure to high energy radiation, and heat treatments.

Unfortunately, the level of sterilisation achieved in these cases is only temporary and must be renewed by repeated treatments both during and after use of the devices. In other words, sterilisation provided by known procedures is not permanent and the material, after initial use, must be subjected to a new sterilisation cycle before it can be re-used.

In conclusion, it would be of great interest to make available materials which themselves have a bactericidal and sterilising action, suitable for the production of articles and devices usable in the medical field or in any other field where long-term sterilisation of the surfaces of articles and devices is required, and which are able to exert a sustained action.

SUMMARY OF THE INVENTION

The Applicant has now surprisingly found that the phthalocyanine derivatives of general formula (I) given hereinafter, having antimicrobial activity, can be immobilised on the surface of polymers, while maintaining their antimicrobial activity.

Subject of the invention is therefore a polymeric product comprising a polymer bound to a phthalocyanine derivative of general formula (I)

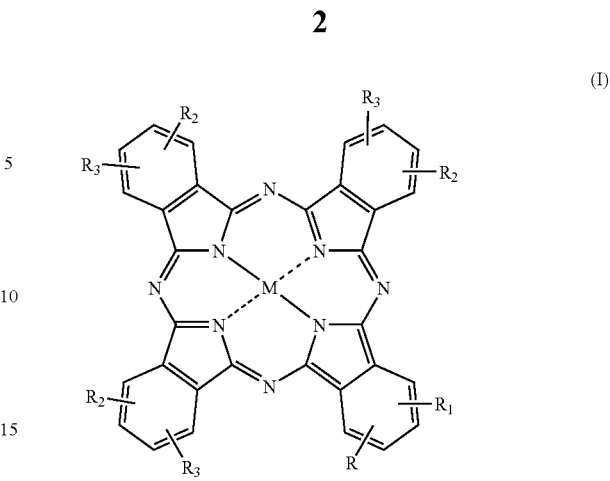

in which M is selected from 2H and a metal selected from the group consisting of Zn, Si(OR')$_2$, Ge(OR')$_2$ and AlOR', where R' is selected from H and alkyl groups having from 1 to 15 carbon atoms.

R is selected from H, groups comprising at least one quaternary ammonium substituent, groups comprising at least one aliphatic amino substituent, and groups suitable for conjugation to specific carriers, $R_1$, equal or different from R, is selected from H, groups comprising at least one aliphatic amino substituent, and groups comprising at least one quaternary ammonium substituent, $R_2$ and $R_3$, equal or different from each other, are selected from H, alkoxy groups having from 1 to 10 carbon atoms, thioalkoxy groups having from 1 to 10 carbon atoms, groups comprising at least one aliphatic amino substituent and groups comprising at least one quaternary ammonium substituent, with the proviso that:

a) at least one of R, $R_1$, $R_2$ and $R_3$ is a group comprising at least one aliphatic amino substituent or a group comprising at least one quaternary ammonium substituent and, when R, $R_1$, $R_2$ and $R_3$ are groups comprising at least one aliphatic amino substituent or groups comprising at least one quaternary ammonium substituent, or R and $R_2$ are groups comprising at least one aliphatic amino substituent or groups comprising at least one quaternary ammonium substituent and $R_1$ and $R_3$ are H, said groups comprising at least one aliphatic amino substituent or said groups comprising at least one quaternary ammonium substituent, are the same;

b) when R and $R_1$ are both different from H, they are in positions 1,4 or 2,3, whereas when only one of R and $R_1$ is different from H, it is in position 1 or 2;

c) when $R_2$ and $R_3$ are both different from H, they are in positions 8, 11, 15, 18, 22, 25 or 9, 10, 16, 17, 23, 24 whereas when only one of $R_2$ and $R_3$ is different from H, it is in positions 8(11), 15(18), 22(25) or in positions 9(10), 16(17), 23(24), and their pharmaceutically acceptable salts.

Further subjects of the invention are also a process for preparing the aforesaid polymeric product, its use for the production or coating of self-sterilising industrial and medical articles or devices, as well as said articles and devices having at least one surface comprising the aforesaid polymeric product.

The characteristics and advantages of the invention will be illustrated in detail in the following description.

BRIEF DESCRIPTION OF THE FIGURES

FIG. 1: concentration (μM) of Compound 9 recovered after desorption with DMF vs. concentration (mM) in the solution for preparing the coating, as in Example 13.

DETAILED DESCRIPTION OF THE INVENTION

Phthalocyanine derivatives are known as photosensitising molecules useful in the well-known photodynamic therapy (or "PDT") for the treatment of both tumours and microbial infections. Phthalocyanines have in fact long been known as compounds able to localise in living eukaryotic or prokaryotic species, and to absorb light to produce reactive oxygen species (ROS), in particular radicals and singlet oxygen, thus destroying cells involved in the photodynamic process (Ben-Hur E. et al. in *Int. J Radiat. Biol.*, Vol 47, pp. 145-147, 1985).

Examples of phthalocyanine derivatives prepared by the Applicant are described in U.S. Pat. No. 5,965,598. These products are used for preparing pharmaceutical compositions useful in the treatment of microbial infections, in the form of solutions for parenteral administration or in the form of creams, gels, ointments and lotions for topical administration, but to date have never been used bound to, or combined with, polymers suitable for the production of articles and devices. The characteristics of the macrocycle and the presence of the substituents strongly influence the production of reactive oxygen species (ROS), and therefore their capacity to induce microbial inactivation.

The production of reactive oxygen species (ROS) is also strongly dependent on the environment where the phthalocyanine is found. In particular, the higher the concentration and therefore the aggregation of phthalocyanine in solution, the less efficient will be its action in the photosensitising process. A negative effect on their photosensitising effect has also been observed when the substituents on the phthalocyanine nuclei have reduced mobility, for example due to steric impedance.

Surprisingly, by using the phthalocyanine derivatives of the invention and the preparation methods, the Applicant has found that their antimicrobial activity, mediated by the production of reactive oxygen species (ROS), is still efficient after immobilisation of the phthalocyanine derivatives on the polymer surface. In particular, the Applicant has observed that, when "modified" by the present phthalocyanines of general formula (1), the surface of the polymer in contact with the micro-organisms becomes self-sterilising.

The present polymeric products are also effective in inactivating bacterial biofilms, complex and well-organised heterogeneous systems able to colonise catheters, prosthetic cardiac valves, dental prostheses and other abiotic surfaces, but also biological tissues such as human tissues, specifically tissues with lesions as in the case of an infected wound, and chronic ulcers.

Biofilms exhibit unique phenotype characteristics when compared with cells in plankton state; in particular, they are several orders of magnitude more resistant to the most common antimicrobial therapies because of multiple resistance mechanisms which render chronic infections associated with bacterial biofilms very difficult to eradicate.

In the present invention, the expression "antimicrobial activity" means and includes both bacteriostatic activity and bactericidal activity. Specifically, the present polymeric products are effective against Gram+ and Gram− bacteria, as well as fungi, mycoplasmas, protozoa, helminths and viruses.

Depending on the phthalocyanine derivative used and its concentration at the polymer surface, antimicrobial activity can be expressed by exposing the surface to visible light, or even in the absence of irradiation. In the first case, antimicrobial activity is maintained for the whole time light is present, and is restored when light again irradiates the surface after a period in darkness. The molecules of the invention are able to effectively absorb visible light at intensity of daylight or artificial lighting. The UV-Vis spectrum shows two bands of strong absorbance around 400 nm and 700 nm, i.e. in the visible region of the light spectrum, and both light sources can therefore be used for irradiating the polymer or the materials to be sterilised.

When the antimicrobial activity of the present products is expressed by exposure to visible and consequently low-energy light, it does not have noxious effects nor does it cause alterations in the properties of the materials to be sterilised.

Since they are effective under non-irradiation conditions, the present polymeric products have the additional advantage that prostheses, stents and similar medical articles intended for use in the internal parts of the human body can be produced with the present products, and their use within the body, and therefore in the absence of visible light, does not compromise their self-sterilising properties.

In accordance with the invention, the expression "group comprising at least one quaternary ammonium substituent or an aliphatic amino substituent" means preferably a $(X)_p R_4$ group, in which X is selected from the group consisting of O, —$CH_2$—, CO, S, SO, and —$NR_5$ where $R_5$ is selected from H and $C_1$-$C_{15}$ alkyl; and $R_4$ is

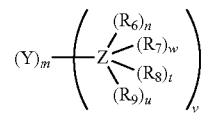

in which

Y is selected from the group consisting of $C_1$-$C_{10}$ alkyl and phenyl, possibly substituted, or Y forms with the Z group to which it is bound, a saturated or unsaturated heterocycle, possibly substituted, which may comprise up to 2 heteroatoms selected from the group consisting of N, O and S;

Z is selected from the group consisting of —N, —$CH_2N$ and —$CONHCH_2CH_2N$;

$R_6$ and $R_7$, equal or different from each other, are selected from the group consisting of $C_1$-$C_{15}$ alkyl and phenyl, or form with the Z group to which they are bound, a saturated or unsaturated heterocycle, possibly substituted, which may comprise up to two heteroatoms selected from the group consisting of N, O and S;

$R_8$ and $R_9$, equal or different from each other, are selected from the group consisting of H, $C_1$-$C_{15}$ alkyl, and $R_{10}COOEt$ or $R_{10}COOMe$ groups in which $R_{10}$ is $C_1$-$C_{15}$ alkyl;

m, n, p, w, t and u, independently from one another, are 0 or 1; and v is an integer between 1 and 3, with the proviso that only one of n, w, t and u is simultaneously 0.

According to the invention, of the groups comprising at least one quaternary ammonium substituent, those selected from the following groups are preferred:

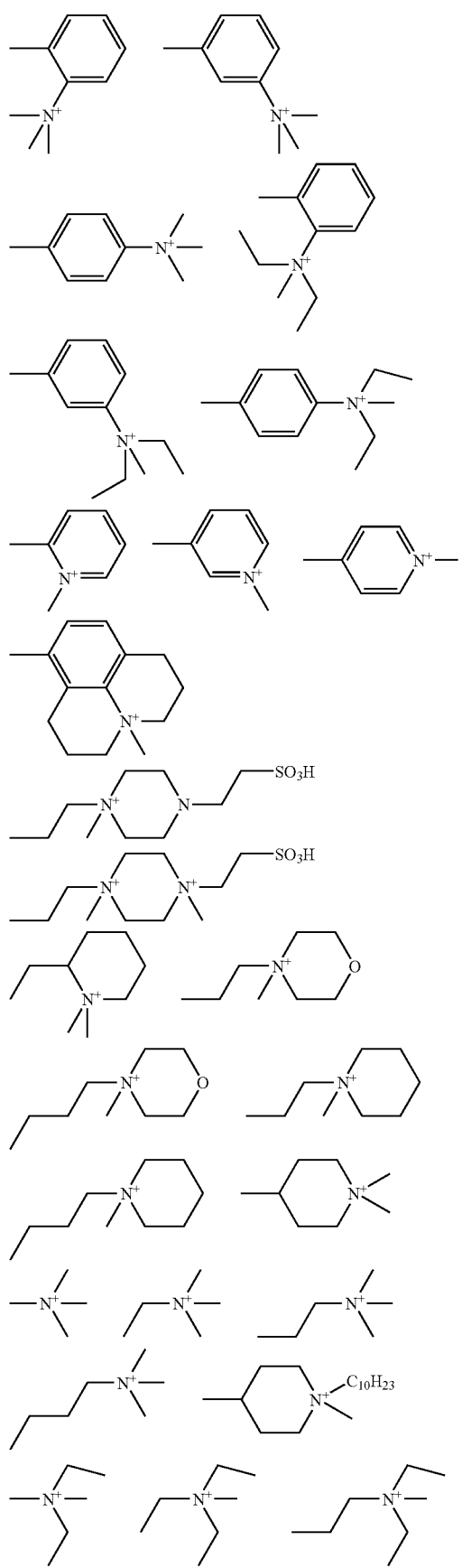
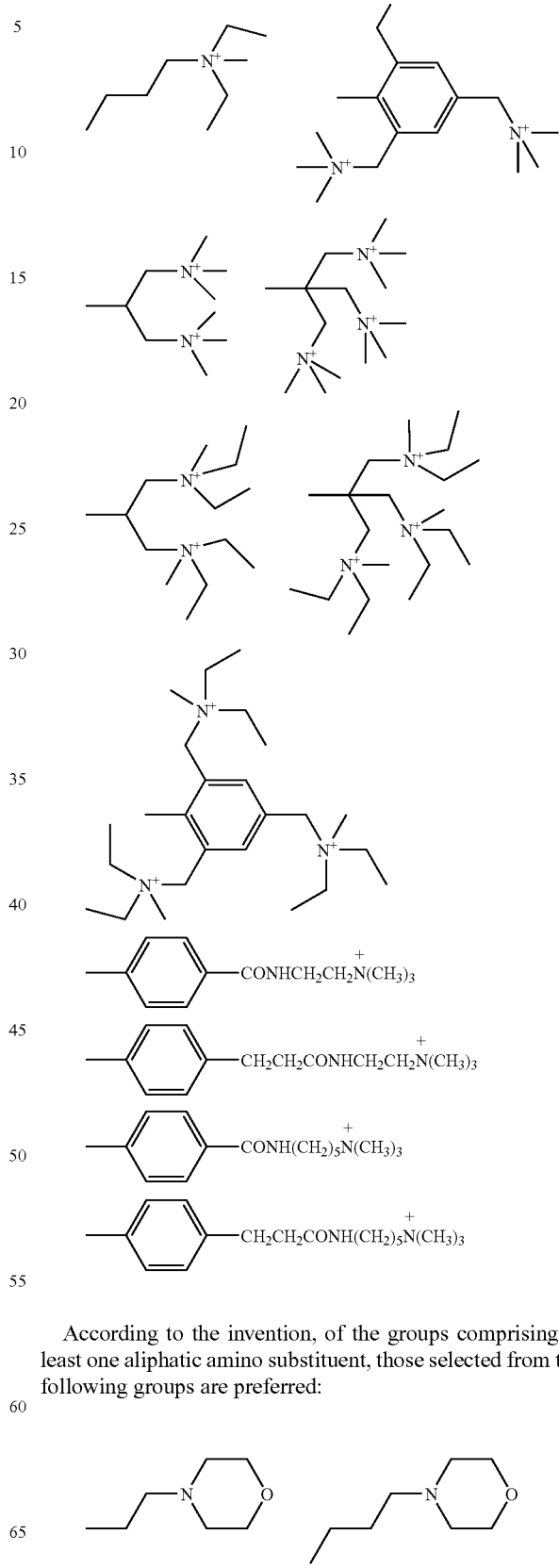
According to the invention, of the groups comprising at least one aliphatic amino substituent, those selected from the following groups are preferred:

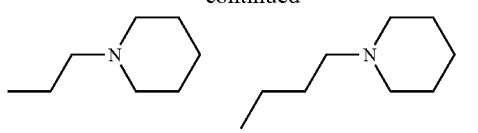
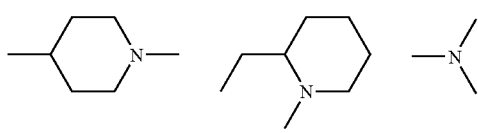
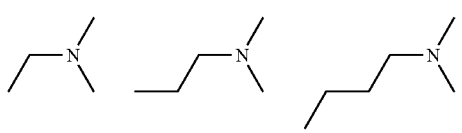
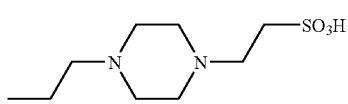
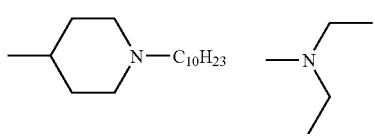
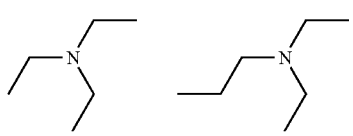
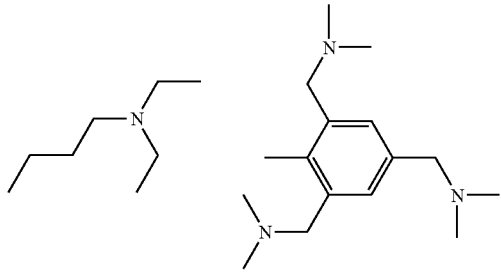
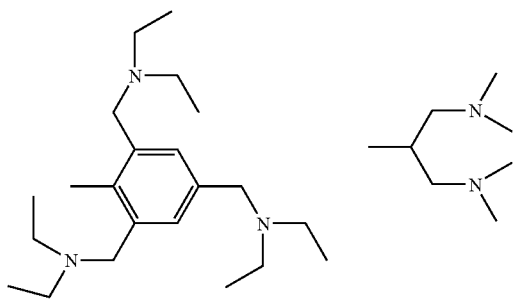
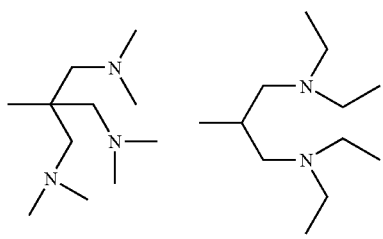
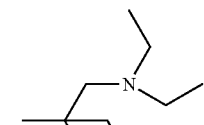
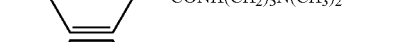
As groups comprising at least one aliphatic amino substituent, the following groups are particularly preferred:
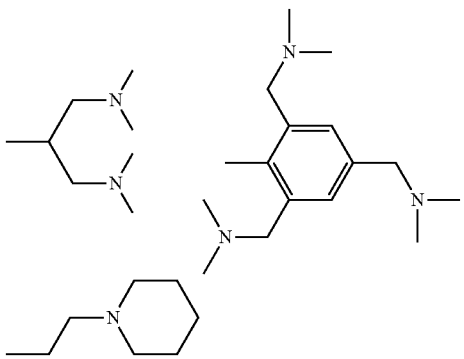
As groups comprising at least one quaternary ammonium substituent, the following groups are particularly preferred:
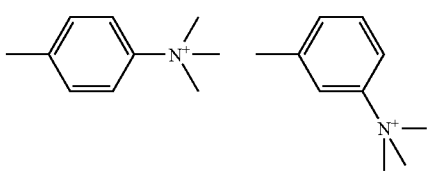

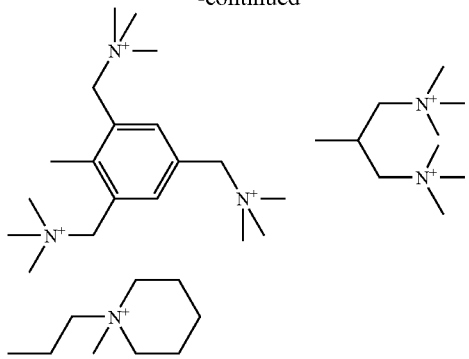

According to a preferred embodiment of the invention, M is Zn.

The term "saturated or unsaturated heterocycle" means preferably a heterocycle selected from the group consisting of morpholine, piperidine, pyridine, pyrimidine, piperazine, pyrrolidine, pyrroline, imidazole, aniline and julolidine.

The term "group suitable for conjugation to specific carriers" means any group suitable for covalently binding to bioorganic carriers such as amino acids, polypeptides, proteins, polysaccharides and aptamers, able to facilitate binding of the described phthalocyanines to solid phases; the aforesaid expression preferably indicates a group selected from the group consisting of —COOH, —SH, —NH$_2$, —CO—CH$_2$—Br, —SO$_2$Cl, maleimide, hydrazine, phenol, imidate, biotin, possibly bound to the phthalocyanine nucleus through a suitable spacer (X)$_p$—W, in which X and p are as defined above and W is selected from C$_1$-C$_{10}$ alkyl, aryl, and C$_1$-C$_5$ arylalkyl.

When R is a group suitable for conjugation to specific carriers, as defined above, R$_1$ is preferably equal to H and R$_2$ and R$_3$ are selected from H, groups comprising at least one aliphatic amino substituent, and groups comprising at least one quaternary ammonium substituent, provided that at least one of R$_2$ and R$_3$ is different from H.

The phthalocyanine derivatives of formula (I) can be prepared from the corresponding amino derivatives, which in turn can be prepared from commercially available products by known procedures, as those described in U.S. Pat. No. 5,965,598, in European Patent No. 1 164 135 and in European Patent No. 1 381 611, all in the name of the Applicant.

The polymers included in the present products can be selected from materials insoluble in water and in biological fluids.

Examples of suitable polymers according to the invention, which can be synthetic or natural include, but are not limited to, cotton, viscose, polystyrene, polyethylene, polypropylene, polyacrylamide, polyamide, polyvinyl alcohol, polysaccharides, cellulose esters such as cellulose acetate, silicon derivatives and mixtures thereof; they can be processed into solid, fibre, textile or film form.

Polymers soluble in water and in biological fluids, such as dextrans and their derivatives, proteins and their methylated derivatives, protein hydrolysates and the like, can be included in the present products, in addition to the aforesaid insoluble polymers, in mixture therewith or as coatings thereon.

The products of the invention can be used in processes for producing and coating articles or devices for use in the medical field and in industry, which present, by virtue of the phthalocyanine derivatives, a surface with self-sterilising characteristics.

The aforesaid articles or devices include, but are not limited to, catheters, guide tubes, probes, cardiac valves, prostheses for soft tissues, prostheses of animal origin, artificial tendons, bone and cardiovascular replacements, contact lenses, blood oxygenators, artificial kidneys, hearts, pancreases and livers, blood bags, syringes, surgical instruments, filtering systems, laboratory instruments, containers for cultures and for cellular and tissue regeneration, supports for peptides, proteins and antibodies, clinical aids for domestic and hospital use, containers and instruments for cosmetic use.

The self-sterilising products of the invention can be used for the production of articles, including complex articles, and coatings, films and fibres; the fibres can be then transformed into textiles, knitted or used for producing non-woven textiles, useful for example for dressings and bandages for wounds.

The present products can also comprise one or more pharmaceutically active substances, for example a substance selected from the group consisting of antibiotics, anti-infectives, antimicrobials, antivirals, cytostatics, antitumor agents, anti-inflammatories, cicatrizants for wounds, anaesthetics, cholinergic or adrenergic agonists or antagonists, antithrombotics, anticoagulants, haemostatics, fibrinolytics, thrombolytic agents, proteins or fragments thereof, peptides, polynucleotides, growth factors, enzymes and vaccines.

The present phthalocyanine derivatives can be physically and/or covalently bound to the polymer. As an alternative, the surface can be pre-treated and the immobilisation can be carried out on the material used for the pre-treatment.

The present products can be prepared by reacting the phthalocyanine derivative (I) with the monomer, then undertaking the polymerisation, or, alternatively, reacting the previously prepared polymer with the phthalocyanine derivative (I).

The specific reaction conditions depend on the polymer surface and on the nature of the substituents on the phthalocyanine nuclei, but in each case the reaction can be carried out by using commonly used techniques well known to any expert in the field.

The phthalocyanine derivatives of formula (I) can be bound to the polymer surface directly or through a spacer; in this case a suitable bifunctional agent is used, such as carbodiimides, glutaraldehyde, 1,1'-carbonyldiimidazole chlorotriazine, cyanogen bromide, mixed anhydrides, imidoesters and maleimido derivatives; otherwise a dopant is used, for example acid reagents such as acrylic acid incorporated into the polymer or added in a second step.

In an additional embodiment of the invention, the polymer surface is first coated with a protein solution so that the phthalocyanine can be immobilised on the protein coating, using either physical or chemical methods.

As an alternative, the phthalocyanine is bound by means of a carboxylic group to amino derivatives of the polymer, allowing an amide group to form.

Alternatively, other functionalities can also be introduced into the photosensitising compound by use of the appropriate chemistry: for example, carboxyethyl groups, useful for enabling immobilisation using physical methods, can alternatively be hydrolysed and the resulting carboxylic function activated by conversion to the corresponding acid chloride, azide or activated ester and then incorporated into the polymeric product, having nucleophilic substituents, using chemical methods well known in the art.

In each case the reaction is carried out between a polymer (or a monomer) optionally coated or derivatized, and a phthalocyanine solution, prepared in turn by dissolving the phthalocyanine of formula (I) or a salt thereof, for example the iodide or chloride, in a suitable solvent.

The quantity of the phthalocyanine derivative bound to the polymer surface has been optimised, to attain concentrations variable within a wide range of values.

Photoinactivation of the micro-organisms depends on the quantity of phthalocyanine present, which can vary according to the level of photobactericidal and sterilising activity required.

To obtain an efficient self-sterilising product, the phthalocyanine concentration in solution can vary for example between 10 µM and 10 mM, being preferably 1 mM.

There are several advantages associated with the use of the present products compared with known sterilisation methods: the production of reactive oxygen species (ROS) involved in the sterilisation process can be easily controlled by varying the concentration of photosensitiser on the surface, the intensity of light and type of light used: irradiation can be undertaken with artificial light as well as with natural light or selecting the wavelength within the visible region of the spectrum. A further advantage is that to achieve sterilisation, specific devices or instruments are not required, neither are repeated treatments with a traditional sterilising agent.

The following non-limiting examples of the present invention are given by way of illustration.

EXAMPLE 1

Preparation of the Diiodide of the Phthalocyanine Derivative of Formula (I) in which M is Zn, $R_1=R_2=R_3=H$, and R=1,3-bis-(trimethylammonium)-2-propyloxy in Position 2 [Compound 1]

0.272 g of 4-[1,3-bis-(dimethylamino)-2-propyloxy]-1,2-benzenedicarbonitrile (1 mmol) and 0.384 g of 1,2-benzenedicarbonitrile (3 mmol) are dissolved in a small quantity of methanol; to the obtained solution $Zn(AcO)_2$ (0.176 g; 0.96 mmol) and DBU (0.66 ml; 0.42 mmol) are added. The mixture is heated to 150° C. under inert atmosphere for 3 hours and 30 minutes. The blue mixture is dissolved in DMF and re-precipitated several times with basic water, then purified by flash chromatography on silica gel, eluting with $Et_2O$/DMF (4:1), EtOAc/DMF (4:1), EtOAc/DMF (1:1), EtOAc/DMF (1:2), and DMF.

The product thus obtained is the compound of formula (I) in which M is Zn, $R_1=R_2=R_3=H$ and R=1,3-bis-(dimethylamino)-2-propyloxy in position 2 [Compound 1bis]; 10 mg of this product (0.014 mmol) are dissolved in 2.5 ml of N-methyl-2-pyrrolidone and treated with excess MeI and the reaction mixture stirred at room temperature for 15 hours.

The product is precipitated with $Et_2O$ from the mixture, recovered by filtration and purified by washing the precipitate several times with organic solvents, thus obtaining the desired product 2[1,3-bis-(trimethylammonium)-2-propyloxy]zinc (II) phthalocyanine diiodide; blue powder.

UV-vis (DMF) $\lambda_{max}(\epsilon, M^{-1}, cm^{-1})$: 343, 607, 672 (1.9275× $10^5$)

$^1$H-NMR (300 MHz, DMSO-$d_6$): δ (ppm)=9.95-9.40 (m, 7H), 9.23 (s, 1H), 8.42-8.35 (m, 6H), 8.25-8.15 (m, 1H), 6.30-6.10 (m, 1H), 4.45-4.10 (m, 4H), 3.55 (s, 18H).

ESI-MS: m/z 375.3$[M-2I]^{2+}$

EXAMPLE 2

Preparation of the Octaiodide of the Phthalocyanine Derivative of Formula (I) in which M is Zn, $R_1=R=H$, and $R=R_3$=1,3-bis-(dimethyl-ethylacetate-ammonium)-2-propyloxy in Positions 2, 9(10), 16(17), 23(24) [Compound 2]

The title compound is prepared by following the procedure previously described in Example 1, starting from 4-[1,3-bis-(dimethylamino)-2-propyloxy]-1,2-benzenedicarbonitrile to obtain the compound of formula (I) wherein M is Zn, $R_1=R_2=H$, and $R=R_3$=1,3-bis-(dimethylamino)-2-propyloxy in positions 2, 9(10), 16(17), 23(24) [Compound 2bis].

0.5 ml of $ICH_2COOEt$ are added to a solution of 5 mg of this amino derivative in 1 ml of N-methylpyrrolidone, and the mixture is left under stirring for 3 days. The product is then precipitated with $Et_2O$, and the solid is washed several times with ether to remove the reaction solvent and impurities.

The product is finally taken up with DMF, precipitated with $Et_2O$ and washed several times with $Et_2O$ and $CHCl_3$.

$^1$H-NMR (300 MHz, DMSO-$d_6$) δ (ppm) 9.5 (t, 4H, J=8.5 Hz), 9.1 (m, 4H), 6.2 (m, 4H), 4.7 (m, 16H), 4.4-4.3 (b.m., 16H), 4.0 (q, 16H, J=6.8 Hz), 3.5 (s, 48H), 1.0 (t, 24H, J=6.8 Hz).

$^{13}$C-NMR (300 MHz, DMSO-$d_6$) δ (ppm)=165.3 156.1 153.1 140.8 134.5 125.0 120.7 112.5 69.6 65.4 62.7 53.8 39.3 14.2

UV-vis (DMF) $\lambda_{max}(\epsilon, M^{-1}, cm^{-1})$: 678, 354.

EXAMPLE 3

Preparation of the Diiodide of the Phthalocyanine Derivative of Formula (I) in which M is Zn, $R_1=R_2=R_3=H$, and R=1,3-bis-(dimethyl-ethylacetate-ammonium)-2-propyloxy in Position 2 [Compound 3]

By following the same procedure as previously described in Example 2, the title compound was prepared; the results of the NMR analysis on the compound thus obtained are given below:

$^1$H-NMR (300 MHz, DMSO-$d_6$) δ (ppm) 9.5-9.3 (m, 6H), 9.1 (s, 2H), 8.1-8.3 (m, 7H), 6.2 (m, 1H), 4.75 (m, 4H), 4.5 (b.d., 2H, J=12 Hz), 4.3 (b.d., 2H, J=12 Hz), 4.05 (q, 4H, J=10 Hz), 3.5 (s, 12H), 1.0 (t, 6H, J=10 Hz).

$^{13}$C-NMR (300 MHz, DMSO-$d_6$) δ (ppm) 165.4 155.9 154.2 154.0 153.8 153.4 140.9 138.6 134.3 130.6 124.9 123.2 120.9 112.1 69.3 65.6 62.8 53.5 39.3 14.2.

EXAMPLE 4

Preparation of the Octaiodide of the Phthalocyanine Derivative of Formula (I) in which M is Zn, $R_1=R_2=H$, and $R=R_3$=1,3-bis-(dimethyl-(2-hydroxycarbonyl)ethyl-ammonium)-2-propyloxy in Positions 2, 9(10), 16(17), 23(24) [Compound 4]

By following the same procedure as previously described in Example 2 but by using as alkylating agent $ICH_2COOH$, the corresponding acid derivative was obtained.

EXAMPLE 5

Preparation of the Diiodide of the Phthalocyanine Derivative of Formula (I) in which M is Zn, $R_1=R_2=R_3=H$, and R=1,3-bis-(dimethyl-(2-hydroxycarbonyl)ethyl-ammonium)-2-propyloxy in Position 2 [Compound 5]

By following the same procedure as previously described in Example 3 but by using as alkylating agent $ICH_2COOH$, the corresponding acid derivative was obtained.

EXAMPLE 6

Preparation of the Triiodide of the Phthalocyanine Derivative of Formula (I) in which M is Zn $R_1=R_3=H$, R=4-hydroxycarbonylphenoxy in Position 2, and $R_2=$[3-(N,N,N-trimethylammonium)phenoxy] in positions 9(10), 16(17), 23(24) [Compound 6]

By following the same procedure as previously described in Example 1 but by using as starting materials [4-(4-hydroxycarbonyl)-phenoxy]-phthalonitrile and 4(-3-dimethylaminophenoxy)-phthalonitrile, the title compound of formula (I) was obtained.

EXAMPLE 7

Preparation of the Triiodide of the Phthalocyanine Derivative of Formula (I) in which M is Zn, $R_1=R_3=H$, R=4-hydroxycarbonylphenoxy in Position 2, and $R_2=$[3-(N,N,N-trimethylammonium)phenoxy] in positions 8(11), 15(18), 22(25) [Compound 7]

By following the same procedure as previously described in Example 1 but by using as starting materials [4-(4-hydroxycarbonyl)-phenoxy]-phthalonitrile and 3(-3-dimethylaminophenoxy)-phthalonitrile, the title compound of formula (I) was obtained.

EXAMPLE 8

Preparation of the Tetraiodide of the Phthalocyanine Derivative of Formula (I) in which M is Zn, $R_1=R_3=H$, $R=R_2=$[3-(N,N,N-trimethylammonium)phenoxy], with R and $R_2$ in Positions 2,9(10),16(17), 23(24) [Compound 8]

a) Synthesis of 2,9(10),16(17),23(24)-tetra[3-(N,N-dimethylamino)phenoxy] Zinc phthalocyaninate [Compound 8bis]

DBU (29 ml-194 mmol) and anhydrous $Zn(OAc)_2$ (3.48 g -19 mmol) were added to 3-(N,N-dimethylamino)phenoxy] phthalonitrile (10 g -38 mmol); the mixture thus obtained was brought to 160° C. and maintained at this temperature for 4 hours, under stirring, under inert atmosphere and shielded from light. After having returned the mixture to room temperature, it was treated with 200 ml of deionised water and the solid obtained separated and washed with water and methanol. The crude product was then subjected to chromatographic purification (silica gel, $CH_2Cl_2$/MeOH 98/2 v/v ). The eluate containing the desired compound as a mixture of positional isomers was concentrated, dissolved in $CH_2Cl_2$ and reprecipitated from n-hexane to give 7.62 g of an isomerically pure mixture (yield=72%).

UV-Vis (DMF) $\lambda_{max}$ (nm) 681 ($\epsilon$=70300 $M^{-1}$ $cm^{-1}$) 612, 356

$^1$H-NMR (200 MHz, DMSO-$d_6$) δ ppm 9.01-8.90 (m, 4H), 8.51-8.45 (m, 4H), 7.82-7.73 (m, 4H), 7.49-7.36 (m, 4H), 6.85-6.73 (m, 12H), 3.05-3.02 (m, 24H).

$^{13}$C-NMR (300 MHz, DMSO-$d_6$) δ ppm 159.71, 159.47, 158.33, 158.21, 153.06, 152.53, 152.23, 152.03, 151.77, 151.36, 139.91, 132.89, 131.16, 131.02, 124.23, 120.32, 110.76, 109.17, 107.97, 107.83, 104.59

FAB-MS m/z 1117 $[M+H]^+$.

b) Synthesis of 2,9(10),16(17),23(24)-tetra[3-(N,N,N-trimethylammonium)phenoxy] zinc phthalocyaninate tetraiodide An excess of iodomethane (16 ml) was added to a solution of zinc 2,9(10),16(17),23(24)-tetra[3-(N,N-dimethylamino)phenoxy] phthalocyaninate (6.32 g-5.65 mmol) in NMP (158 ml) and the mixture maintained under stirring for 120 hours, at room temperature and shielded from light, then diluted with methanol (320 ml) and treated with ethyl ether (1.3 l) to give a green precipitate corresponding to the desired product in the form of an isomeric mixture (9 g, 95% yield).

UV-Vis (DMF) $\lambda_{max}$(nm) 677 ($\epsilon$=161000 $M^{-1}$ $cm^{-1}$), 609, 353;

$^1$H-NMR (200 MHz, DMSO-$d_6$) δ ppm 9.55-9.43 (m, 4H), 9.09-9.02 (m, 4H), 8.22-8.15 (m, 4H), 8.07-7.76 (m, 12H), 7.62-7.52 (m, 4H) 3.77 and 3.75 (2s, 36H)

$^{13}$C-NMR (200 MHz, DMSO-$d_6$) δppm 157.84, 157.67, 152.50 (m), 148.85, 140.00 (m), 134.00, 131.77, 124.70, 121.30 (m), 120.18, 119.89, 115.99, 115.80, 112.70, 112.42, 56.60

ESI-MS m/z 388 $[M-4I-CH_3]^{3+}$, 573 $[M-4I-2CH_3]^{2+}$, 1132 $[M-4I-3CH_3]^+$.

By using the procedure described above in Example 12 and the process for preparing phthalocyanine derivatives chlorides starting from the corresponding iodides as described in International Patent Application No. PCT/EP2006/062059 in the name of the Applicant, the following phthalocyanine derivatives of formula (I) and corresponding amino derivatives intermediates, were also prepared:

EXAMPLE 9

Tetrachloride of the Phthalocyanine Derivative of Formula (I) in which M is Zn, $R_1=R_3=H$, $R=R_2=$[3-(N,N,N-trimethylammonium)phenoxy], with R and $R_2$ in Positions 1, 8(11), 15(18), 22(25) [Compound 9], and Phthalocyanine derivative of formula (I) in which M is Zn, $R_1=R_3=H$, $R=R_2=$[3-(N,N-dimethylamino)phenoxy] in positions 1, 8(11), 15(18), 22(25) [Compound 9bis]

EXAMPLE 10

Tetrachloride of the phthalocyanine derivative of formula (I) in which M is Zn, $R_1=R_3=H$, $R=R_2=$[4-(N,N,N-trimethylammonium)phenoxy], with R and $R_2$ in positions 1, 8(11), 15(18), 22(25) [Compound 10], and Phthalocyanine derivative of formula (I) in which M is Zn, $R_1=R_3=H$, $R=R_2=$[4-(N,N-dimethylamino)phenoxy] in positions 1,8(11), 15(18), 22(25) [Compound 10bis]

EXAMPLE 11

Octachloride of the phthalocyanine derivative of formula (I) in which M is Zn, $R=R_1=R_2=R_3=$[3-(N,N,N-trimethylammonium)phenoxy], with R, $R_1$, $R_2$, $R_3$ in positions 2,3,9, 10,16,17,23,24 [Compound 11], and Phthalocyanine derivative of formula (I) in which M is Zn, $R=R_1=R_2=R_3=$[3-(N,N-dimethylamino)phenoxy] in positions 2,3,9,10,16,17,23,24 [Compound 11bis]

EXAMPLE 12

Octachloride of the phthalocyanine derivative of formula (I) in which M is Zn, $R=R_1=R_2=R_3=$[3-(N,N,N-methyldiethylammonium)phenoxy], with R, $R_1$, $R_2$, $R_3$ in positions 2,3,9,10,16,17,23,24 [Compound 12], and Phthalocyanine derivative of formula (I) in which M is Zn, $R=R_1=R_2=R_3=$[3-(N,N-diethylamino)phenoxy] in positions 2,3,9,10,16,17,23,24 [Compound 12bis]

EXAMPLE 13

A polystyrene square (2 cm×2 cm, 0.2 cm thick) was immersed in a solution of Compound 1 prepared as described above in Example 1, at a concentration of 1 mM in DMSO and incubated overnight at 4° C. The solution was then removed and the polystyrene extensively washed in ethanol and water. The product thus obtained was dried prior to use.

Similarly, Compounds 2, 3, 8 and 9 were immobilised on polystyrene following this procedure. The extent of loading by coating the Compound 9 prepared as described above in Example 9 in $H_2O/CH_3OH$ (4:1) after overnight incubation at 4° C. onto polystyrene was performed by using Petri dishes made out of this material. The amount of compound adsorbed in polystyrene was evaluated spectrophotometrically (690 nm) by measuring the concentration of Compound 9 after desorption with DMF. Results of solid phase loadings as a function of coating concentration, i.e. concentration of Compound 9 in the starting solution used for the preparation of the coating, are indicated in FIG. 1.

EXAMPLE 14

Lenses made out of Nefilcon A and PVA (Focus Daily, Ciba Vision) and silicon catheters (Sterile double lumen 15-French Nelaton, Maersk Medical Sdn, Malaysia) were coated by Compound 1 prepared as described above in Example 1, by overnight incubation at 4° C. respectively in a solution at 1 mM and 1 µM of Compound 1 in $H_2O/CH_3OH$ (4:1), followed by rinsing with sterile PBS.

EXAMPLE 15

Polystyrene wells were treated with a BSA solution having a concentration of 0.1 mg/ml and incubated for 1 hour at 37° C. The solution was removed, the wells washed with PBS and immediately treated with a solution of Compound 1 prepared as described above in Example 1. The solution was incubated overnight at 4° C., the solution removed and the wells extensively washed with ethanol, water and dried prior to use.

Analogously, Compounds 8-12 described in Examples 8-12 have been linked to polystyrene following the same procedure described above, obtaining the same results.

EXAMPLE 16

Polystyrene wells were treated with a solution of glutaraldehyde (GA) in 0.1% PBS and incubated for 1 hour at 37° C. The GA solution was removed, the wells washed with PBS and immediately treated with a solution of Compound 1bis, prepared as described above in Example 1 at 1 mg/ml. The solution was incubated overnight at 4° C., the solution removed and the wells dried prior to use. In the same way, Compounds 2bis, 8bis, 9bis, 10bis, 11bis and 12bis prepared as described above in Examples 2 and 8-12, were used to the purpose of coating.

EXAMPLE 17

Silicon tubing were treated with a solution of GA in 0.1% PBS and 0.01% human serum albumin (HSA) and incubated for 1 hour at 37° C. The solution was removed, the tubing were washed with PBS and immediately treated with different solutions of Compound 1 prepared as previously described in Example 1 in DMSO and in mixtures $H_2O/CH_3OH$ at various ratios ranging from 10:90 to 90:10.

The solutions were incubated overnight at 4° C., the solutions removed and the tubing washed until no more photosensitized was detected, thus obtaining a tubing having a molecular coating of the photosensitable compound.

Compounds 2, 3 and 8-12 prepared as described above in Examples 2, 3, 8-12 have been used for coating silicon tubing by using the same procedure as described above, obtaining the same results.

EXAMPLE 18

Nylon tubing were superficially partially depolimerized by using a 2 N HCl solution for 3 h at room temperature. The surface was neutralised with a solution of sodium bicarbonate and treated with N-succinimidyl-3-(2-pyridylthio)-propionate (SPDP). After reaction the tubing was extensively washed with ethanol and treated with dithiothreitol 1 mM, to obtain the —SH free form of the reagent immobilised onto Nylon tubing, following the reaction spectrophotometrically by measuring the 2-thiopyridone chromophore.

Compounds 5, 6 and 7 prepared as described above in Examples 5, 6 and 7, previously modified to introduce a maleimido group into the phtalocyanine moiety by using conventional procedures described in Hermanson, *Bioconjugate Techniques,* Academic Press 1996, were used for immobilisation.

The procedure described leads to the covalent attachment of the phthalocyanine derivatives onto the modified surface.

EXAMPLE 19

*Staphylococcus aureus* (strain 6538 ATCC) was grown in Tryptic Soy broth (Difco) at 37° C. under aerobic conditions. Cells were taken from the culture during the stationary growth phase, washed twice with PBS and diluted in the same buffer to $1×10^4$. Sterile contact lenses (Focus Daily, Ciba Vision) made from Nelficon A and PVA and sterile double lumen 15-French Nelaton (Maersk Medical Sdn, Malaysia) catheters made from silicon prepared according to Example 14, were used.

Contact lenses or catheters sections were placed into 6-well tissue culture plates and 2 ml of *S. aureus* suspension were added in each well. The culture plates were incubated for 5 minutes at 37° C. and then irradiated (600-700 nm, 30 $J/cm^2$).

After irradiation, 100 µl taken from the well suspensions were ten fold serially diluted and plated onto Tryptic soy agar (TSA). TSA plates were incubated for 24 h at 37° C., colonies were counted and their numbers expressed as CFU/ml.

Test controls were also performed on untreated devices.

All experiments were carried out three to five times, and the results are summarised in the following Tables 1 and 2.

TABLE 1

| Medical devices | Mean bacterial density ($\log_{10}$ CFU/ml) ± SD Irradiated | |
|---|---|---|
| | Control | Treated |
| Catheters | 4.36 ± 0.14 | 0.25 ± 0.31 |
| Lenses | 4.38 ± 0.03 | 1.05 ± 0.50 |

TABLE 2

| Medical devices | Mean bacterial density ($\log_{10}$ CFU/ml) ± SD Not irradiated | |
|---|---|---|
| | Control | Treated |
| Catheters | 4.38 ± 0.08 | 3.92 ± 0.54 |
| Lenses | 4.42 ± 0.13 | 3.76 ± 0.04 |

The invention claimed is:

1. A polymeric product comprising a polymer bound, directly or through a spacer, to a phthalocyanine derivative of general formula (I):

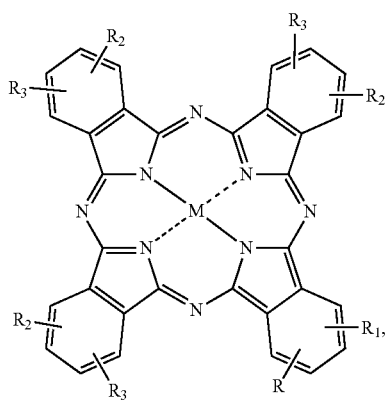

wherein said phthalocyanine derivative of general formula (I) is selected from the group of compounds consisting of:

Diiodide of the phthalocyanine derivative of formula (I) in which M is Zn, $R_1=R_2=R_3=H$, and R=1,3-bis-(trimethylammonium)-2-propyloxy in position 2 [Compound 1];

Octaiodide of the phthalocyanine derivative of formula (I) in which M is Zn, $R_1=R_2=H$, and $R=R_3=1,3$-bis-(dimethyl-ethylacetate-ammonium)-2-propyloxy in positions 2, 9(10), 16(17), 23(24) [Compound 2];

Diiodide of the phthalocyanine derivative of formula (I) in which M is Zn, $R_1=R_2=R_3=H$, and R=1,3-bis-(dimethyl-ethylacetate-ammonium)-2-propyloxy in position 2 [Compound 3];

Octaiodide of the phthalocyanine derivative of formula (I) in which M is Zn, $R_1=R_2=H$, and $R=R_3=1,3$-bis-(dimethyl-(2-hydroxycarbonyl)ethyl-ammonium)-2-propyloxy in positions 2, 9(10), 16(17), 23(24) [Compound 4];

Diiodide of the phthalocyanine derivative of formula (I) in which M is Zn, $R_1=R_2=R_3=H$, and R=1,3-bis-(dimethyl-(2-hydroxycarbonyl)ethyl-ammonium)-2-propyloxy in position 2 [Compound 5];

Triiodide of the phthalocyanine derivative of formula (I) in which M is Zn, $R_1=R_3=H$, R=4-hydroxycarbonylphenoxy in position 2, and $R_2$=[3-(N,N,N-trimethylammonium) phenoxy] in positions 9(10), 16(17), 23(24) [Compound 6];

Triiodide of the phthalocyanine derivative of formula (I) in which M is Zn, $R_1=R_3=H$, R=4-hydroxycarbonylphenoxy in position 2, and $R_2$=[3-(N,N,N-trimethylammonium) phenoxy]iodide in positions 8(11), 15(18), 22(25) [Compound 7];

Tetraiodide of the phthalocyanine derivative of formula (I) in which M is Zn, $R_1=R_3=H$, $R=R_2$=[3-(N,N,N-trimethylammonium)phenoxy] in positions 2,9(10), 16(17), 23(24) [Compound 8];

Tetrachloride of the phthalocyanine derivative of formula (I) in which M is Zn, $R_1=R_3=H$, $R=R_2$=[3-(N,N,N-trimethylammonium)phenoxy] in positions 1, 8(11), 15(18), 22(25) [Compound 9];

Tetrachloride of the phthalocyanine derivative of formula (I) in which M is Zn, $R_1=R_3=H$, $R=R_2$=[4-(N,N,N-trimethylammonium)phenoxy] in positions 1, 8(11), 15(18), 22(25) [Compound 10];

Octachloride of phthalocyanine derivative of formula (I) in which M is Zn, $R=R_1=R_2=R_3$=[3-(N,N,N-trimethylammonium)phenoxy] in positions 2,3,9,10,16, 17,23,24 [Compound 11]; and Octachloride of the phthalocyanine derivative of formula (I) in which M is Zn, $R=R_1=R_2=R_3$=[3-(N,N,N-methyldiethylammonium)phenoxy] in positions 2,3, 9,10,16,17,23,24 [Compound 12].

2. The polymeric product according to claim 1, wherein said polymer is mixed with or coated with a polymer soluble in water or in biological fluids.

3. The polymeric product according to claim 2, wherein said polymer is selected from the group consisting of viscose, polystyrene, polyethylene, polypropylene, polyacrylamide, polyamide, polyvinyl alcohol, polysaccharides, cellulose esters, cellulose acetate, silicon derivatives and mixtures thereof.

4. The polymeric product according to claim 2, wherein said soluble polymer is selected from the group consisting of dextrans and their derivatives, proteins and their methylated derivatives, and protein hydrolysates.

5. The polymeric product according to claim 1, wherein said spacer comes from the linkage of said phthalocyanine derivative and said polymer by a suitable bifunctional agent selected from the group consisting of carbodiimides, glutaraldehyde, 1,1'-carbonyldiimidazole chlorotriazine, cyanogen bromide, mixed anhydrides, imidoesters and maleimido derivatives.

6. Self-sterilizing industrial and medical articles and devices produced or coated with the polymeric product as defined in claim 1.

7. Articles and devices according to claim 6 in combination with one or more pharmaceutically active substances.

8. Articles and devices according to claim 6 having at least one surface coated with the polymeric product.

9. Articles and devices according to claim 6, selected from the group consisting of catheters, guide tubes, probes, cardiac valves, prostheses for soft tissues, prostheses of animal origin, artificial tendons, bone and cardiovascular replacements, contact lenses, blood oxygenators, artificial kidneys, hearts, pancreases and livers, blood bags, syringes, surgical instruments, filter systems, laboratory instruments, containers for cultures and for cellular and tissue regeneration, supports for peptides, proteins and antibodies, clinical aids for domestic and hospital use, containers and instruments for cosmetic use.

10. The polymeric product according to claim 1, wherein said polymer is selected from the group consisting of viscose, polystyrene, polyethylene, polypropylene, polyacrylamide, polyamide, polyvinyl alcohol, polysaccharides, cellulose esters, cellulose acetate, silicon derivatives and mixtures thereof.

11. The polymeric product of claim 1, wherein said phthalocyanine derivative of formula I is selected from the group of compounds consisting of:

Diiodide of the phthalocyanine derivative of formula (I) in which M is Zn, $R_1=R_2=R_3=H$, and R=1,3-bis-(trimethylammonium)-2-propyloxy in position 2[Compound 1];

Tetraiodide of the phthalocyanine derivative of formula (I) in which M is Zn, $R_1=R_3=H$, $R=R_2=$[3-(N,N,N-trimethylammonium)phenoxy] in positions 2, 9(10), 16(17), 23(24) [Compound 8]; and Tetrachloride of the phthalocyanine derivative of formula (I) in which M is Zn, $R_1=R_3=H$, $R=R_2=$[3-(N,N,N-trimethylammonium)phenoxy] in positions 1, 8(11), 15(18), 22(25) [Compound 9].

\* \* \* \* \*